United States Patent
Liu et al.

(10) Patent No.: US 7,192,780 B2
(45) Date of Patent: Mar. 20, 2007

(54) FLUORESCENT LIFETIME BIOLOGICAL DETECTION AND IMAGING USING WATER-STABLE SEMICONDUCTOR NANOCRYSTALS

(75) Inventors: Wei Liu, Guilderland, NY (US); Zuoyan Peng, Guilderland, NY (US); Michael LoCascio, Albany, NY (US)

(73) Assignee: Evident Technologies, Troy, NY (US)

( * ) Notice: Subject to any disclaimer, the term of this patent is extended or adjusted under 35 U.S.C. 154(b) by 205 days.

(21) Appl. No.: 10/885,867

(22) Filed: Jul. 8, 2004

(65) Prior Publication Data

US 2005/0251027 A1 Nov. 10, 2005

Related U.S. Application Data

(63) Continuation-in-part of application No. 10/616,975, filed on Jul. 11, 2003, now Pat. No. 6,872,450.

(60) Provisional application No. 60/485,243, filed on Jul. 8, 2003, provisional application No. 60/420,534, filed on Oct. 23, 2002.

(51) Int. Cl.
*G01N 33/00* (2006.01)
*G01N 33/53* (2006.01)
*C07H 21/04* (2006.01)
*C12Q 1/68* (2006.01)

(52) U.S. Cl. .............. 436/94; 436/800; 435/6; 536/23.1; 536/24.31

(58) Field of Classification Search ............... 435/6, 435/91.1, 91.2, 287.2; 436/94, 800; 536/23.1, 536/24.31
See application file for complete search history.

(56) References Cited

U.S. PATENT DOCUMENTS

| | | | |
|---|---|---|---|
| 6,251,303 B1 | 6/2001 | Bawendi et al. | |
| 6,274,323 B1 * | 8/2001 | Bruchez et al. | 435/6 |
| 6,306,610 B1 * | 10/2001 | Bawendi et al. | 435/7.1 |
| 6,319,426 B1 | 11/2001 | Bawendi et al. | |
| 6,426,513 B1 | 7/2002 | Bawendi et al. | |
| 6,444,143 B2 | 9/2002 | Bawendi et al. | |
| 6,602,671 B1 | 8/2003 | Bawendi et al. | |
| 6,617,583 B1 | 9/2003 | Bawendi et al. | |
| 6,774,361 B2 | 8/2004 | Bawendi et al. | |

* cited by examiner

*Primary Examiner*—Bradley L. Sisson
(74) *Attorney, Agent, or Firm*—Kenyon & Kenyon LLP (57) ABSTRACT

A method of detecting target biological molecules in a target sample is provided. The method includes using spectral, temporal, and polarization characteristics of emitted light from water-stable semiconductor nanocrystal complexes to detect the presence of target biological molecules in a target sample.

6 Claims, 5 Drawing Sheets

FLUORESCENT LIFETIME BIOLOGICAL DETECTION AND IMAGING USING WATER-STABLE SEMICONDUCTOR NANOCRYSTALS

CROSS-REFERENCE TO RELATED APPLICATIONS

This present application is a continuation-in-part of U.S. patent application Ser. No. 10/616,975, filed on Jul. 11, 2003, now U.S. Pat No. 6,872,450 which claims priority to U.S. Provisional Application No. 60/420,534, filed on Oct. 23, 2002. This application also claims priority to U.S. Provisional Application No. 60/485,243, filed on Jul. 8, 2003. All the foregoing are incorporated by reference herein.

FIELD OF THE INVENTION

The present invention relates generally to fluorescence lifetime imaging and spectroscopy using surface-modified semiconductor nanocrystal complexes that are water-stable. The present invention relates, in particular, to use of said fluorescence lifetime techniques for biological detection and imaging applications.

BACKGROUND OF THE INVENTION

Fluorescence imaging is particularly powerful because the use of fluorescent labels can yield a high specificity and because appropriate analysis of the fluorescence signal can provide information about the environment of the fluorophore molecules as well as their location. Although fluorescence imaging is a long-established technique, recent advances in both label and detection technology are radically enhancing its impact in biomedicine. For cell biology, genomics, and proteomics, for example, the use of fluorescence labels allows biologists to observe the location of specific oligonucleotides in an assay or proteins in living cells. For medical imaging, fluorescence can provide greater specificity than absorption- or scattering-based techniques because it can derive functional contrast from intrinsic autofluorescence and/or from exogenous fluorescence labels. As the understanding of cell biology, immunology and proteomics grows, the techniques developed for these research agendas will increasingly be applied directly in clinical practice. In particular, we are now seeing rapid growth in techniques to realize in vivo microscopy and high-resolution endoscopy, optical imaging tools that will make use of fluorescence to provide functional contrast.

Fluorescence microscopy, in which the sample absorbs incident photons and emits light (fluorescence) at different (longer) wavelengths, is a well-established way of providing contrast that is not achievable with reflected light microscopy. Since the wavelength of the emitted fluorescence depends on the energy level structure of the fluorescent molecules (or "fluorophores"), it may be used to distinguish different molecular species in a sample. Thus, qualitative imaging of fluorescence intensity can reveal the location or distribution of fluorophores and spectrally resolved intensity imaging can contrast different fluorophores if their fluorescence emission spectra are sufficiently different. In biological samples, almost all the constituents will exhibit fluorescence if excited at an appropriate wavelength. For example, ultraviolet radiation can excite many organic molecules. This is often a problem since the aim is usually to study one or two specific biological entities and normally the excitation wavelength is carefully chosen so that it only excites the molecular species of interest. At longer wavelengths, in the visible and near infrared, it is not always possible to find an excitation wavelength to excite a given biological sample—particularly given the lack of tunable visible lasers suitable for microscopy. In many cases it is convenient to label the biological target with a fluorescent molecular species that can be excited using a convenient light source. Fluorophore labels are usually selected for their high fluorescence efficiencies and for their potential to be localized or attached to the biological targets in the sample. The latter issue is nontrivial and has engaged the attention of the biology and chemistry communities for many decades.

Quantitative imaging of fluorescence intensity can furnish functional information about a sample since the efficiency of the fluorescence process can reveal information about the fluorophore and its local environment. Fluorescence efficiency is conveniently parametenzed by the quantum efficiency $\eta$, defined as $\Gamma/(\Gamma+k)$, where $\Gamma$ and $k$ are, respectively, the radiative and nonradiative decay rates. The quantum efficiency may also be described as the ratio of the number of fluorescence photons emitted to the number of excitation photons absorbed. The radiative decay rate is related to the transition oscillator strength, while the nonradiative decay rate can vary according to how the fluorophore interacts with its local environment. For some fluorophores, $k$ is sensitive to the local pH, or to calcium ion concentration, or to physical factors such as viscosity. For this reason, fluorescent "probes" may be employed to produce functional maps of perturbations in such environmental factors by recording distributions of changes in $k$ using quantitative fluorescence intensity imaging. In heterogeneous biological samples, however, it can be difficult to measure quantum efficiency because of possible artifacts arising from, for example, nonuniform fluorophore concentration, excitation flux or detection efficiency. Optical scattering can also degrade quantitative intensity measurements. For carefully prepared thin samples, one can assume that some of these factors are uniform across the field of view but for thick samples, and particularly for in vivo imaging, it is often not possible to reliably determine quantum efficiency. A more robust approach is to make relative intensity measurements at each pixel in the field of view. One approach is to employ special probes with fluorescence spectra that change in a predictable way according to the strength of the local environmental perturbation—the concentration of $Ca^{+2}$ ions, for example. By incorporating such probes into a sample and recording fluorescence intensity images at two or more wavelengths, it may be, for example, possible to produce a map of $Ca^{+2}$ concentration distributions in order to study signaling in nerve synapses. Such spectrally resolved relative measurements could effectively eliminate factors caused by optical scattering and noise from background fluorescence, as well as nonuniformity in fluorophore concentration, excitation and detection efficiency. "Wavelength-ratiometric imaging" has been successfully applied to microscopy and to in vivo diagnostic imaging. Unfortunately, this technique is limited to those instances for which suitable wavelength-ratiometric probes (or endogenous fluorophores) are available, currently a significant restriction.

Another way of obtaining functional information from relative intensity measurements (or images) is to temporally resolve fluorescence profiles after pulsed (or modulated) excitation. Just as spectral discrimination adds both a new dimension to fluorescence data and enhanced opportunities for contrast and robust functional imaging, the application of temporal resolution adds yet another dimension. Fluorescence lifetime imaging (FLIM) involves determining the average fluorescence decay time for each pixel in the field of view and producing a map (or series of maps) of lifetime data. Like the quantum efficiency, η, the fluorescence lifetime (τ) depends on both the radiative and nonradiative decay rates. Like η, it can be used to contrast different fluorophore species (via k) and different local fluorophore environments (via k). FLIM thus provides a robust functional imaging modality that may be applied to any fluorescent sample, and it is currently being applied to biological samples ranging from single cells to bulk tissue. FLIM is also attracting growing interest among researchers active in the field of microanalysis of sample arrays and high-throughput screening.

Water-stabilized nanocrystals capable of conjugating to probe molecules are particularly attractive for fluorescence based biological imaging and detection because they have a continuously selectable wavelength emission (i.e. many colors are realizable). Probe molecules have a specific affinity toward a target molecule and include proteins, avidin, streptavidin, biotin, nucleic acids, antibodies, enzymes, aptamers, oligonucleotides etc. The resultant nanocrystal tagged probe is used in a biological assay to optically identify the presence of a target molecule within the sample. Evident Technologies Inc. has recently demonstrated that water-stabilized nanocrystals are ideally suited for fluorescence lifetime imaging as well. All nanocrystal populations, despite their average size (which determines the emission wavelength) have nearly the same fluorescence lifetime of 15–20 nanoseconds (ns). This lifetime is very large when compared to the fluorescence lifetime of organic fluorophores and especially when compared the autofluorescence lifetime of organic molecules within a sample. Thus, using water-stabilized nanocrystal complexes coupled to a specific binding molecule, one can perform a biological assay or image using a time resolved detection platform that has an enhanced signal to noise ratio over that of conventional fluorescence detection methodologies.

Semiconductor nanocrystals are tiny crystals of II–VI, III–V, IV–VI materials that have a diameter typically between manometer (nm) and 20 nm. In the strong confinement limit, the physical diameter of the nanocrystal is smaller than the bulk exciton Bohr radius causing quantum confinement effects to predominate. In this regime the nanocrystal has both quantized density and energy of electronic states where the actual energy and energy differences between electronic states are a function of both the nanocrystal composition and physical size. Larger nanocrystals have more closely spaced energy states and smaller nanocrystals the reverse. Because interaction of light and matter is determined by the density and energy of electronic states, many of the optical and electric properties of nanocrystals can be tuned or altered simply by changing the nanocrystal geometry (i.e. physical size).

Single nanocrystals or monodisperse populations of nanocrystals exhibit unique optical properties that are size tunable. Both the onset of absorption and the fluorescence wavelength are a function of nanocrystal size and composition. The nanocrystals will absorb all wavelengths shorter than the absorption onset and emit light (at a wavelength corresponding to the absorption onset. The bandwidth of the fluorescence spectra is due to both homogeneous and inhomogeneous broadening mechanisms. Homogeneous mechanisms include temperature dependent Doppler broadening and broadening due to the Heisenburg uncertainty principle, while inhomogeneous broadening is due the size distribution of the nanocrystals. Populations of nanocrystal with a narrow size distribution have, as a result, a narrow FWHM of emission spectra. The quantum yield (i.e. the percent of absorbed photons that are reemitted as photons) is influenced largely by the surface quality of the nanocrystal. Photoexcited charge carriers will emit light upon direct recombination but will give up the excitation energy as heat if phonon or defect mediated recombination paths are prevalent. Because the nanocrystal has a large surface area to volume ratio, dislocations present on the surface or adsorbed surface molecules having a significant potential difference from the nanocrystal itself will tend to trap excited state carriers and prevent radiative recombination and thus reduce quantum yield. Quantum yield can be increased by removing surface defects and separating adsorbed surface molecules from the nanocrystal by adding a shell of a semiconductor with a wider bulk bandgap than that of the core semiconductor.

Hines and Guyot-Sionest developed a method for synthesizing a ZnS shell around a CdSe core nanocrystal. See Hines M., Guyot-Sionnest P., *Synthesis and Characterization of Strongly Luminescent ZnS-Capped CdSe Nanocrystals, J. Phys. Chem.,* 1996, vol. 100, no. 2, pp. 468, incorporated by reference herein. The CdSe cores, having a monodisperse distribution between 2.7 nm and 3.0 nm (i.e. 5% size distribution with average nanocrystal diameter being 2.85 nm), were produced using the Katari and Alivisatos variation of the Murray synthesis. The photoluminescence spectra of the core show a FWHM of approximately 30 nm with a peak at approximately 540 nm. The core CdSe nanocrystals were separated, purified, and resuspended in a TOPO solvent. The solution was heated and injected with Zinc and Sulphur precursors (Dimethyl Zinc and $(TMS)_2S$) to form a ZnS shell around the CdSe cores. The resultant shells were 0.6±0.3 nm thick, corresponding to 1–3 monolayers. The photoluminescence of the core-shell nanocrystals had a peak at 545 nm, FWHM of 40 nm, and a quantum yield of 50%.

One problem, however, is that semiconductor nanocrystals are inherently insoluble in any solvent and require a coating with suitable functional groups to enable suspension. Therefore, coatings having hydrophilic groups are required for water solubility. Those same hydrophilic groups also act as anchoring sites to couple the nanocrystal to a tertiary molecule such as a protein, antibody, nucleic acid, polymer etc. Short chain thiols such as 2-mercaptoethanol and 1-thioglyceral have been used as stabilizers in the preparation of water-soluble CdTe nanocrystals. See Rajh et al., *Synthesis and Characteristics of Surface-Modified Colloidal CdTe Quantum Dots, J. Phys. Chem.,* vol. 97, No. 46, 11999–12003, 1993; Rogach et al, *Synthesis and Characterization of Thiol-Stabilized CdTe Nanocrystals, Ber. Bunsenges. Phys. Chem,* vol. 100, No. 11, 1772–1778, 1996, incorporated by reference herein. Bawendi et al., describes a method of preparing water soluble nanocrystals that do not demonstrate a reduction on quantum yield using long chain multidentate thiols, however the nanocrystals will precipitate when dialyzed indicating a lack of tight binding to the nanocrystal surface. See U.S. Pat. No. 6,319,426, entitled "Water-Soluble Fluorescent Semiconductor Nanocrystals," incorporated by reference herein. It is important to note that in biological assays that require the nanocrystal to couple to a probe molecule, the lack of tight coupling between the probe molecule and the nanocrystal surface will inevitably lead to the probe molecule becoming disassociated resulting in inaccurate results of the assay.

SUMMARY OF THE INVENTION

In an embodiment, the present invention provides a method of detecting at least one target biological molecule in a target sample. The method comprises providing at least one water-stable semiconductor nanocrystal complex. The at least one complex comprises a semiconductor nanocrystal, a moiety having an affinity for a surface of the semiconductor nanocrystal, a hydrophilic group, and a tertiary molecule coupled to the hydrophilic group and capable of binding to the at least one target biological molecule. The method further comprises exposing the at least one complex to a target sample containing the at least one target biological molecule and exposing the sample to a light source that causes the at least one complex to emit light having a fluorescent lifetime. The method moreover comprises terminating exposure of the target sample to the light source, and measuring the fluorescent lifetime of the emitted light of the complex to determine whether hydridization of the target biological molecule to the at least one complex has occurred.

In another embodiment, the present invention provides a method of detecting at least one target biological molecule in a target sample comprising providing at least one water-stable semiconductor nanocrystal complex that is capable of emitting light. The at least one complex comprises a semiconductor nanocrystal, a moiety having an affinity for a surface of the semiconductor nanocrystal, a hydrophilic group, and a tertiary molecule coupled to the hydrophilic group and capable of binding to the at least one target biological molecule. The method further comprises determining a first fluorescent lifetime of the emitted light of the at least one complex and exposing the at least one complex to a target sample, the target sample containing the at least one target biological molecule. The method moreover comprises measuring a second fluorescent lifetime of the emitted light of the at least one complex, wherein a difference between the first and second fluorescent lifetimes indicates hybridization of the target biological molecule to the at least one complex.

In another embodiment, the present invention provides a method of detecting at least one target biological molecule in a target sample comprising providing at least one water-stable semiconductor nanocrystal complex that is capable of emitting light having an anisotropy of polarization. The at least one complex comprises a semiconductor nanocrystal, a moiety having an affinity for a surface of the semiconductor nanocrystal, a hydrophilic group, and a tertiary molecule coupled to the hydrophilic group and capable of binding to the target biological molecule. The method moreover comprises exposing the at least one complex to polarized light and determining a first anisotropy of polarization of the emitted light of the at least one complex. The method moreover comprises exposing the at least one complex to a target sample containing the at least one target biological molecule and then re-exposing the at least once complex to polarized light. The method further comprises detecting a second anisotropy of polarization of the emitted light of the at least one complex, wherein a difference between the first and second anisotropies of polarization indicates hybridization of the target biological molecule to the at least one complex.

In yet another embodiment, the present invention provides a method of detecting at least one target biological molecule in a target sample comprising providing at least one water-stable semiconductor nanocrystal complex that is capable of emitting fluorescent light. The at least one complex comprises a semiconductor nanocrystal, a moiety having an affinity for a surface of the semiconductor nanocrystal, a hydrophilic group and a tertiary molecule coupled to the hydrophilic group and capable of binding to the target biological molecule. The method further comprises exposing the at least one complex to a target sample containing the at least one target biological molecule and exposing the target sample to a light source that causes the at least one complex to emit fluorescent light. The method moreover comprises detecting whether fluorescent light is emitted by the at least one complex, wherein emission of fluorescent light indicates hybridization of the target biological molecule to the at least one complex.

DETAILED DESCRIPTION OF THE INVENTION

In general, the present invention relates to use of water-stable semiconductor nanocrystal complexes in fluorescent lifetime imaging apparatuses for biological assays and cellular imaging.

Figure 1:
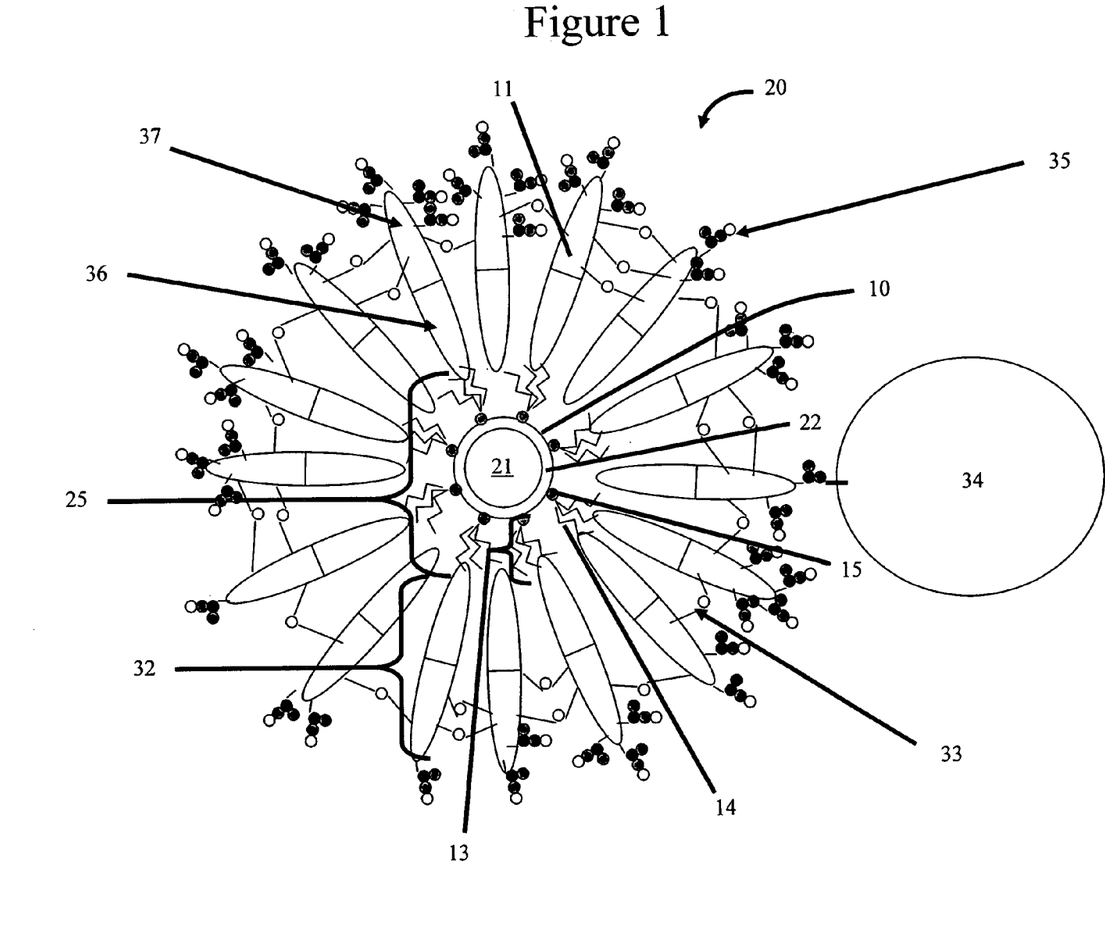
FIG. 1 is a schematic illustration of an embodiment of a surfactant coated semiconductor nanocrystal complex according to the present invention.

Referring to FIG. 1, in an embodiment, a semiconductor nanocrystal complex 20a comprises a semiconductor nanocrystal 10 that is coated with lyophilic surfactant molecules 13, which in turn are coated with an organic layer 11 to form a micelle. As is generally known in the art, semiconductor nanocrystals are spherical nanoscale crystalline materials (although oblate and oblique spheroids can be grown as well as rods and other shapes) having a diameter between 1 nm and 20 nm and typically but not exclusively composed of II–VI, III–V, and IV–VI binary semiconductors. Semiconductor nanocrystal 20 according to the present invention includes a core 21 of a first semiconductor that has a selected composition and diameter that enables light emission at a predetermined wavelength and optionally a shell 22 of a second semiconductor having a bulk bandgap greater than that of the first semiconductor of core 21. Optional shell 22 is preferably between 0.1 nm and 10 nm thick and composed of a semiconductor material that has a lattice constant that matches or nearly matches core 21. Non-limiting examples of semiconductor materials comprising core 21 and shell 22 include ZnS, ZnSe, ZnTe, CdS, CdSe, CdTe, HgS, HgSe, HgTe (II–VI materials), PbS, PbSe, PbTe (IV–VI materials), AlN, AlP, AlAs, AlSb, GaN, GaP, GaAs, GaSb, InN, InP, InAs, InSb (III–V materials).

Surfactant molecules 13 that coat semiconductor nanocrystal 10 of the present invention are generally organic molecules that have a moiety 15 with an affinity for the surface of semiconductor nanocrystal 10 and a moiety 14 with an affinity for a hydrophobic solvent. Non-limiting examples of moiety 15 include thiols, amines, phosphines, phosphine oxides, and any combinations thereof. Non-limiting examples of surfactant molecules 13 include trioctyl phosphine oxide (TOPO), trioctyl phosphine (TOP), tributyl phosphine (TBP), dodecyl amine, octadecyl amine, hexadecylamine, stearic acid, oleic acid, palmitic acid, lauric acid, and any combinations thereof. Such surfactant molecules 13 are typically used in the synthesis of semiconductor nanocrystals and can remain on the surface of the nanocrystals after synthesis or may be added or replaced by other surfaces after synthesis. As is generally known to one of skill in the art, semiconductor nanocrystals 10 according to the present invention may be coated with surfactant molecules 13 by pyrolysis of organometallic precursors in a chelating ligand solution or by an exchange reaction using the prerequisite salts in a chelating surface solution, such chelating surfaces typically being lyophilic. Surfactant molecules 13 according to the present invention tend to assemble into a coating around semiconductor nanocrystal 10 forming a surface-coated semiconductor nanocrystal 25 and enable it to suspend in a hydrophobic solvent.

Semiconductor nanocrystal complex 20a further comprises an organic layer 11, which surrounds surface-coated semiconductor nanocrystal 25 to form a micelle through self-assembly. Organic layer 11 is typically comprised of cross-linked or uncross-linked molecules or polymers having one or more hydrophobic regions or groups and one or more hydrophilic regions or groups. Non-limiting examples of organic layer 11 include soaps, detergents, fatty acids, lipids, phospholipids, sphingolipids, polyethylene glycol, amphipathic copolymers, and amphiphilic polymers such as amphiphilic diblock polymers.

Referring again to FIG. 1, in a preferred embodiment, organic layer 11 comprises a layer of amphiphilic diblock polymers 32 that assemble around surface-coated semiconductor nanocrystal 25 to render nanocrystal 25 water-soluble. More than one surface-coated semiconductor nanocrystal 25 may be surrounded by the diblock polymer coating 32. A diblock polymer 32 is generally but not exclusively a linear chain that has a hydrophobic end 36 comprising hydrophobic functional groups that is covalently bonded to a hydrophilic end 37 comprising hydrophilic functional groups. In an aqueous medium, the layer of diblock polymers 32 assembles around surface-coated semiconductor nanocrystal 25 of the present invention. Specifically, hydrophobic end 36 of diblock polymer 32 is attracted to surface-coated nanocrystal 25 and interacts with moiety 14 of surfactant molecule 13 through noncovalent interactions such as, for example, hydrogen bonding, Van der Waals Forces, and hydrophobic interactions. Hydrophilic end 37 of diblock polymer 32, in turn, is directed to the aqueous medium.

The hydrophobic functional groups of hydrophobic end 36 are preferably groups of covalently bonded atoms on a larger molecule that are nonpolar and not ionizable and therefore have an affinity for nonpolar and nonionizable solvents. Non-limiting examples of hydrophobic functional groups according to the present invention include hydrocarbons of various lengths. The hydrophilic functional groups of hydrophilic end 37 are preferably groups of atoms on a larger molecule that are highly polar or ionizable and therefore have an affinity for water and other polar solvents. Non-limiting examples of hydrophilic functional groups include hydroxy, amine, carboxyl, sulfonates, phosphates, amines, nitrates, and any combinations thereof.

With respect to the lengths of hydrophobic end 36 and hydrophilic end 37 of diblock polymer 32, each end has lengths greater than 1 and preferably each have lengths between 1 and 1000. In a more preferred embodiment, hydrophobic end 36 of diblock polymer 32 has between 60 and 180 carbon atoms. In a more preferred embodiment, hydrophobic end 36 has about 150 carbon atoms and hydrophilic end 37 has about 220–240 carbon atoms. Also in a preferred embodiment, hydrophobic end 36 has about 10–20 monomer units and hydrophilic end 37 has about 110–120 monomer units. Although hydrophilic end 37 and hydrophobic end 36 may have different lengths, in a preferred embodiment they are substantially equal in length.

Non-limiting examples of diblock polymers 32 that may surround surfactant-coated semiconductor nanocrystal according to the present invention include poly(acrylic acid-b-methyl methacrylate), poly(methyl methacrylate-b-sodium acrylate), poly(t-butyl methacrylate-b-ethylene oxide), poly(methyl methacrylate-b-sodium methacrylate), poly(methyl methacrylate-b-N-methyl 1-4vinyl pyridinium iodide), poly(methyl methacrylate-b-N,N-dimethyl acrylamide), poly(butadiene-b-methacrylate acid and sodium salt), poly(butadiene(1,2 addition)-b-acrylic acid), poly(butadiene(1,2 addition)-b-sodium acrylate), poly(butadiene(1,4 addition)-b-acrylic acid), poly(butadiene(1,4 addition)-b-sodium acrylate), poly(butadiene(1,4 addition)-b-ethylene oxide), poly(butadiene(1,2 addition)-b-ethylene oxide), poly(styrene-b-acrylic acid), poly(styrene-b-acrylamide), poly(styrene-b-cesium acrylate), poly(styrene-b-sodium acrylate), poly(styrene-b-ethylene oxide), poly(styrene-b-methacrylic acid), poly(styrene-b-sodium methacrylate), and any combinations thereof.

In order to form a cohesive coating around surfactant-coated semiconductor nanocrystal of the present invention, adjacent diblock polymers 32 of the diblock polymer layer may be linked together by linking molecules 33. Preferably linking molecules 33 are multidentate linking molecules having one or more reactive functional groups that can react with and bond to one or more hydrophilic functional groups of hydrophilic end 37 thereby crosslinking adjacent diblock polymers 32 together. Therefore, the self-assembled diblock polymer layer is knit together to form a cohesive coating around surfactant-coated semiconductor nanocrystal of the present invention that will not dissociate in water over long periods. The multidentate linking molecule of the present invention may have one or more than one type of reactive functional group. Non-limiting examples of such reactive functional groups include hydroxy (OH), carboxylate (COOH), amine ($NH_2$) groups, and any combinations thereof. In a preferred embodiment, linking molecule 33 is diamine, 2,2'-(ethylenedioxy)bis(ethylamine) and the amine functional groups on the diamine react with hydrophilic functional groups that are carboxylate groups on hydrophilic end 37 of diblock polymer 32 to form a stable peptide bond.

Figure 2:
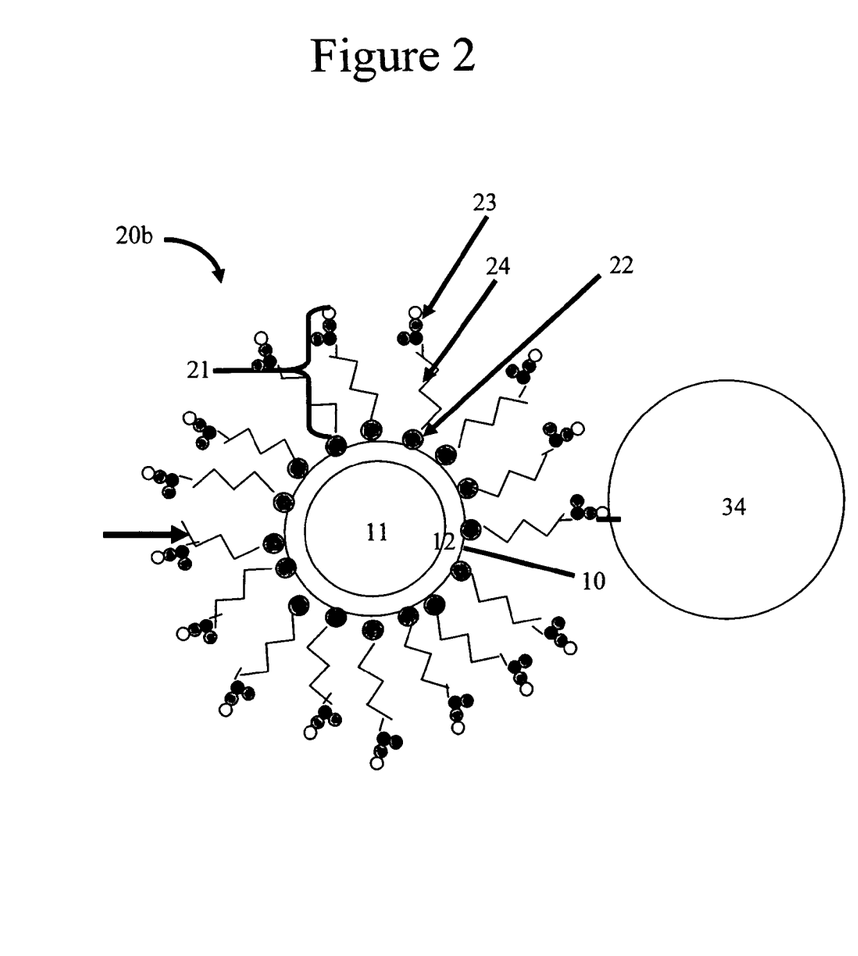
FIG. 2 is a schematic illustration of an embodiment of a semiconductor nanocrystal complexes according to the present invention.
Figure 3:
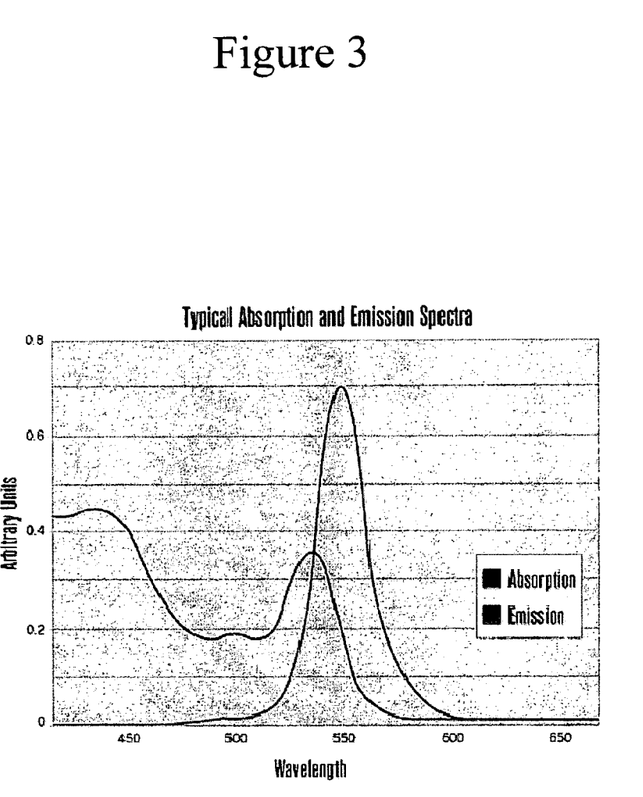
FIG. 3 is a graph showing the absorption spectra and emission spectra of a solution of a monodisperse population of semiconductor nanocrystal complexes according to the present invention.

Referring to FIG. 2, in another embodiment, semiconductor nanocrystal complex 20b comprises a semiconductor nanocrystal 10 that is coated with hydrophilic surfactant molecules 21. Hydrophilic surfactant molecules 21 have one or more moieties 22 with an affinity for the nanocrystal surface and have one or more terminal polar and/or ionizable functional groups 23, which may be same or of different types. Non-limiting examples of moieties 22 include thiols, amines, phosphines, phosphine oxides, nitriles, and carboxy groups. Non-limiting examples of polar and/or ionizable functional groups 23 include amines, carboxys, hydroxys, sulfonats, nitrates, phosphates, and any combination thereof. The polar/ionizable functional groups 23 are separated from moieties 22 by a hydrophobic region 24, where the hydrophobic regions may be a single or multiple hydrocarbon branched or unbranched chains, single or multiple aromatic rings, dendrimers, dendrons, crosslinked or uncrosslinked organosilanes, etc. Non-limiting examples of hydrophilic surfactant molecules 21 include mercaptocarboxylic acid, dimercaptocarboxylic acid, mercapto functionalized amines, trimercaptocarboxylic acids, or diaminocarboxylic acid such as mercapto acetic acid, aminoethanethiol, homocysteine, aminopropanethiol, mercaptoproprionic acid, mercaptobutric acid, mecaptopimelic acid, lysine, cystiene, asparaagine, glutamine, arginine, citrulline, ornithine, hydroxylysine, diaminopentanoic acid, diaminopimelic acid, homocystiene, serine, glycine, threonine, mercaptohexanioc acid, mercpatounadecanoic acid, lipoic acid, triton, mercaptopropyl-trimethoxysilane, aminopropyl-trimethoxysilane, maleimidopropyl-trimethoxysilane, hydrazidopropyl-trimethoxysilane.

Semiconductor nanocrystal complex 20b can be formed by replacing lyophilic surfactants molecules 13 that coat a semiconductor nanocrystal 10 (as are present on surface-coated semiconductor nanocrystal 25 of semiconductor nanocrystal complex 20a) with hydrophilic surfactant molecules 21.

Hydrophilic functional groups present on hydrophilic end 37 of semiconductor nanocrystal complex 20a and polar or ionizable functional groups 23 present on semiconductor nanocrystal 20b can serve as attachment sites for coupling to tertiary molecules or structures 34 (as illustrated in FIGS. 1 and 2). Such tertiary molecules 34 can be coupled to nanocrystal complex 20 via conventional chemistries such as EDC coupling and other chemistries well known to one of skill in the art. Nonlimiting examples of tertiary molecules or structures and specific binding molecules include proteins, enzymes, protein A, protein G, avidin, streptavidin, microtubules, antibodies, oligonucleotides, mRNA, DNA, aptamers, glycopeptides, bacteria, viruses, cellular organelles, liposomes, molecular beacons, biotin, oligomers, polymers, a polypeptide, a nucleic acid, a peptide nucleic acid, a cellular receptor molecule, a receptor-specific ligand, an enzyme cofactor, an oligosaccharide, a lipopolysaccharide, a glycolipid, a lectin, a polymer, a metallic surface, a metallic particle, and any combinations thereof.

Figure 4:
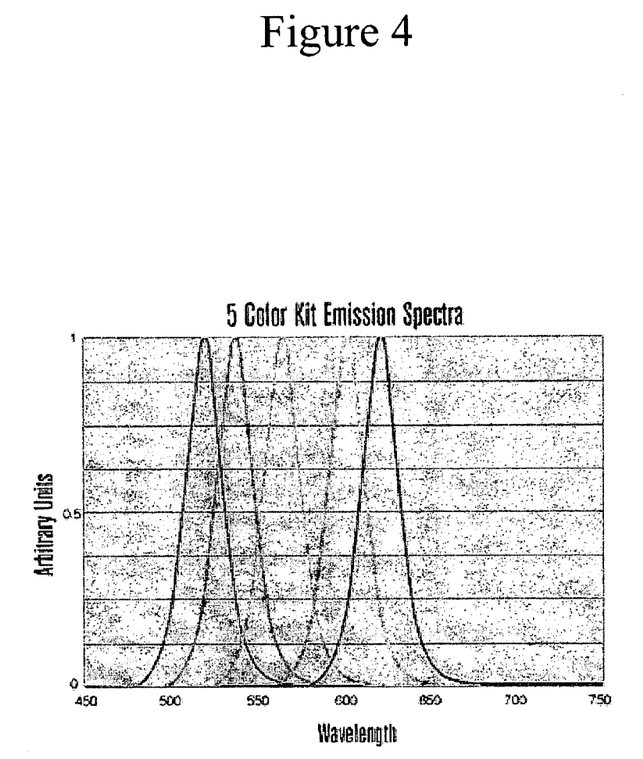
FIG. 4 is a graph showing the emission spectra of five different solutions of mondisperse populations of semiconductor nanocrystal complexes according to the present invention all having different mean diameters.

Nanocrystal complexes 20 of the present invention emit light of a characteristic wavelength when illuminated by a light having a wavelength equal to or less than the emitted light, where the emitted wavelength is dependent upon the composition and size of said nanocrystal, as is generally known in the art. FIG. 4 is an example absorption and emission (fluorescence) spectra of the resultant monodisperse semiconductor nanocrystal complex. Due to quantum confinement, the electronic energy states are quantized. The successive peaks on the absorption spectra correspond to the energy states of the semiconductor nanocrystal complexes. The exhibited emission peak has a narrow full width half maximum (<30 nm) due to small inhomogeneous broadening of a monodisperse population of the nanocrystals in solution. The figure demonstrates that light having a shorter wavelength than the emission light will be absorbed. The figure also demonstrates that the shorter the illumination wavelength the more light will be absorbed and that multiple nanocrystal dispersions can be illuminated by the same short wavelength light source. It is preferable but not necessary that wavelengths less than 400 nm in the UV part of the spectrum are used to illuminate nanocrystal complexes.

FIG. 4 shows the emission spectra of five different monodisperse semiconductor nanocrystal complex solutions. The difference between the solutions is the mean diameters of the suspended semiconductor nanocrystals. The larger nanocrystals have redder emissions while the smaller nanocrystals have bluer emission. The nanocrystals shown have a CdSe core and a coating of ZnS. The ZnS has a wider bandgap than the CdSe core and acts to eliminate defects from the CdSe surface thereby enhancing radiative recombination mechanisms and boosting quantum yields.

Figure 5:
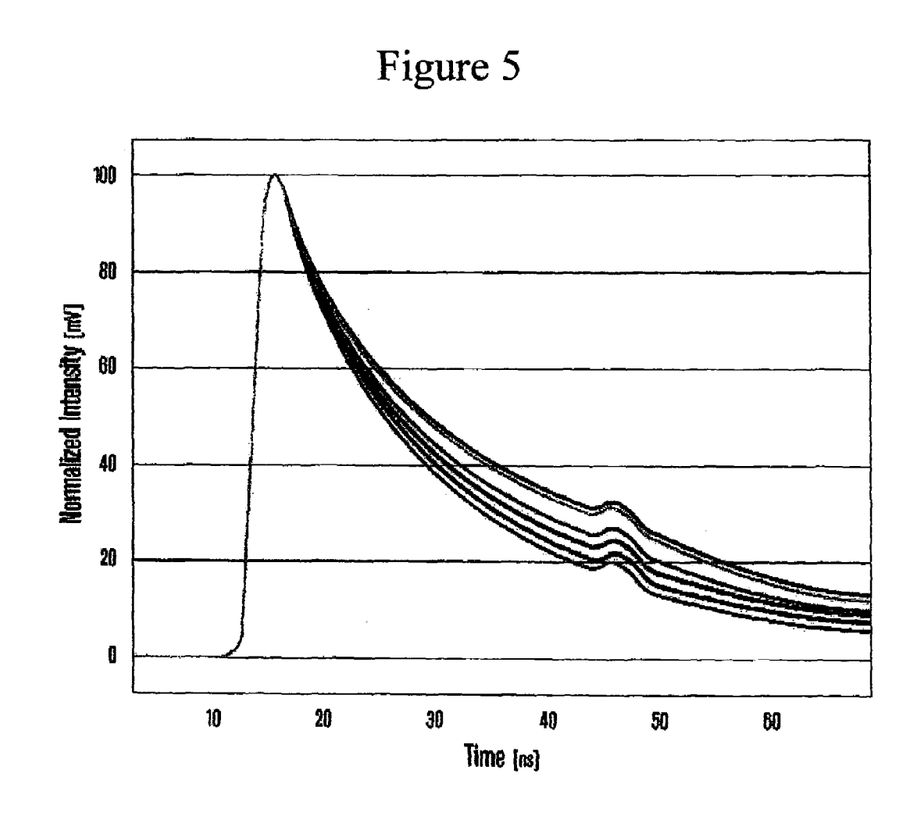
FIG. 5 is a graph showing the fluorescence lifetimes of different monodisperse solutions of semiconductor nanocrystal complexes according to the present invention all having different mean diameters.

If the illuminating lightsource provides the light in short pulses or quickly oscillates the fluorescence lifetime, the emitted light from said nanocrystal complexes can be measured, where fluorescence lifetime is defined as the time required for the emission light intensity to drop in half after the illumination light has been turned off. Measurement apparatuses that provide fluorescence lifetime information (as well as spectral and polarization information) are broken up into two general categories, known as time-correlated single photon counting or frequency domain apparatuses, both of which are known in the art. FIG. 5 shows fluorescence lifetime of 6 solutions of nanocrystal complexes according to the present invention. The difference between the solutions is the mean diameter of the suspended semiconductor nanocrystals. Each of the solutions has nanocrystal complexes that containing nanocrystals composed of a CdSe core and a ZnS shell. The data shows that all the nanocrystal complexes despite their size have approximately the same fluorescence lifetime, ranging from 15 to 20 nanoseconds. This fluorescent lifetime is greater than the 2.8 ns lifetime of Green Fluorescing Protein and similar fluorophores and far greater than the sub nanosecond autofluorescence lifetime characterized by UV illuminated organic molecules.

Many methods of performing assays or cellular/subcellular imaging can be devised that use the temporal characteristics of nanocrystal complexes to either increase the signal to noise ratio of the emitted light over that of background light or detect an environmental change or hybridization event through a change in the fluorescence lifetime of said nanocrystal complexes. In most cases nanocrystal complexes are used that have been conjugated to one or more previously described specific binding molecules. Said nanocrystal complexes conjugated to specific binding molecules can, under the circumstances known the art, hybridize with specific targets or target complexes, where target molecules or target complexes may be fixed to, dispersed in, or floating in a sample. Samples is a general term understood to be, but not limited to, a slide, filter paper, a membrane, or multiwell plate, a cuvette, an electrophoretic a gel as in the case of protein and DNA/RNA assays such as Western, Northern, or Southern Blots, or may be within or part of a cell, a tissue sample. Nonlimiting examples of targets are DNA fragments, mRNA, oligonucleotides, chromosomes, aptamers, organelles, bacteria, virus particles, subcellular structures, membranes, proteins, membrane protein, ribosomes, antibodies, antigens etc. Target complexes are targets that have been conjugated to a detectable label where said label may be, but not limited to, an organic fluorophore, another nanocrystal complex, a microbead, a fluorescence or color barcoded microbead known in the art, a magnetic microbead or nanoparticle, a gold nanoparticle, an oxide nanoparticle, a rare-earth or lanthanide doped oxide nanoparticle, a chemiluminescent enzyme, or a radioactive label etc. In particular, target complexes having a label that will absorb the light emitting from the nanocrystal complex and, in turn, emit a third light at a different wavelength are useful. More particularly, target complexes having a label that upon hybridization with a conjugated nanocrystal complex detectably alter the fluorescence lifetime of the nanocrystal complex by absorbing the light emitted from the nanocrystal complex and emitting a third light of a different wavelength and different fluorescent lifetime.

Both types of fluorescence lifetime detection apparatuses, time correlated single photon counting and the frequency domain technique, include tunable or fixed ultrafast pulsed or sinusoidally modulated lightsource, respectively. The lightsources produce a first light that is directed towards the sample and is capable of causing light emission from nanocrystal complexes within. Nonlimiting examples of lightsources are pulsed lasers such as frequency tripled YAG lasers and modulated blue or UV laser diodes. The light emitted from the nanocrystal complexes within the sample is directed toward photodector, linear photodector array, or 2-d photodetector arrays (for taking images), such as CCDs, via a variety of optics. The photodetectors are typically electrically time gated to yield the temporal response of the light emitted from the sample. Nonlimiting examples of said optics include arthroscopes, endoscopes, optical fiber, optical fiber bundles, confocal microscopes, microscopes, and conventional optics. It should be noted that in the frequency domain technique light emitted from the sample is first passed through an optical component that breaks the light into its spectral components such as a prism or a diffraction grating. In addition, the first light produced by the light source can be polarized by a variety of means known in the art and the polarization of the light emitted from the sample can be measured by the addition of polarizers and dichroic filters that precede the photodetector, also known in the art. By the addition, of tunable filters or other spectral separation components, known in the art, the spectral characteristics as well as the temporal characteristics (and the polarization) of the light emitted from the sample can be measured or imaged.

Nonlimiting examples of fluorescence lifetime measurement techniques include the application of fluorescence lifetime imaging to cellular imaging, wide-field fluorescence lifetime imaging, multispectral fluorescence lifetime imaging that resolves spatial, spectral, and temporal aspects of the emitted light of nanocrystal complexes, endoscopic fluorescence lifetime imaging, fluorescence quenching or fluorescence resonant energy transfer (FRET) measurements, fluorescence lifetime and anisotropy polarization imaging.

The foregoing description and examples have been set forth merely to illustrate the invention and are not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

We claim:

1. A method of detecting at least one target biological molecule in a target sample comprising:
   providing at least one water-stable semiconductor nanocrystal complex, the at least one complex comprising:
      a semiconductor nanocrystal;
      a moiety having an affinity for a surface of the semiconductor nanocrystal;
      a hydrophilic group; and
      a tertiary molecule coupled to the hydrophilic group and capable of binding to the at least one target biological molecule;
   exposing the at least one complex to a target sample containing the at least one target biological molecule;
   exposing the target sample to a light source that causes the at least one complex to emit light having a fluorescent lifetime;
   terminating exposure of the target sample to the light source; and
   measuring the fluorescent lifetime of the emitted light of the complex to determine whether hydridization of the target biological molecule to the at least one complex has occurred.

2. A method of detecting at least one target biological molecule in a target sample comprising:
   providing at least one water-stable semiconductor nanocrystal complex that is capable of emitting light, the at least one complex comprising:
      a semiconductor nanocrystal;
      a moiety having an affinity for a surface of the semiconductor nanocrystal;
      a hydrophilic group; and
      a tertiary molecule coupled to the hydrophilic group and capable of binding to the at least one target biological molecule;
   determining a first fluorescent lifetime of the emitted light of the at least one complex;
   exposing the at least one complex to a target sample, the target sample containing the at least one target biological molecule; and
   measuring a second fluorescent lifetime of the emitted light of the at least one complex, wherein a difference between the first and second fluorescent lifetimes indicates hybridization of the target biological molecule to the at least one complex.

3. The method of claim 1, wherein the at least one target biological molecule is conjugated to a detectable label.

4. The method of claim 1, wherein the light source emits light pulses or light having oscillating intensity.

5. A method of detecting at least one target biological molecule in a target sample comprising:
   providing at least one water-stable semiconductor nanocrystal complex that is capable of emitting light having an anisotropy of polarization, the at least one complex comprising:
      a semiconductor nanocrystal;
      a moiety having an affinity for a surface of the semiconductor nanocrystal;
      a hydrophilic group; and
      a tertiary molecule coupled to the hydrophilic group and capable of binding to the target biological molecule;
   exposing the at least one complex to polarized light;
   determining a first anisotropy of polarization of the emitted light of the at least one complex;
   exposing the at least one complex to a target sample containing the at least one target biological molecule;
   re-exposing the at least once complex to polarized light; and
   detecting a second anisotropy of polarization of the emitted light of the at least one complex, wherein a difference between the first and second anisotropies of polarization indicates hybridization of the target biological molecule to the at least one complex.

6. A method of detecting at least one target biological molecule in a target sample comprising:

providing at least one water-stable semiconductor nanocrystal complex that is capable of emitting fluorescent light, the at least one complex comprising:

a semiconductor nanocrystal;

a moiety having an affinity for a surface of the semiconductor nanocrystal;

a hydrophilic group; and a tertiary molecule coupled to the hydrophilic group and capable of binding to the target biological molecule;

exposing the at least one complex to a target sample containing the at least one target biological molecule;

exposing the target sample to a light source that causes the at least one complex to emit fluorescent light; and detecting whether fluorescent light is emitted by the at least one complex, wherein emission of fluorescent light indicates hybridization of the target biological molecule to the at least one complex.

* * * * *

UNITED STATES PATENT AND TRADEMARK OFFICE
CERTIFICATE OF CORRECTION

PATENT NO. : 7,192,780 B2  Page 1 of 1
APPLICATION NO. : 10/885867
DATED : March 20, 2007
INVENTOR(S) : Liu et al.

It is certified that error appears in the above-identified patent and that said Letters Patent is hereby corrected as shown below:

| Column | Line | |
|---|---|---|
| 2 | 17 | Change "conveniently parametenzed" to --conveniently parameterized--. |
| 3 | 41 | Change "between manometer" to --between 1 nanometer--. |
| 10 | 51 | Change "DNAIRNA" to --DNA/RNA--. |

Signed and Sealed this

Twenty-first Day of August, 2007

JON W. DUDAS
*Director of the United States Patent and Trademark Office*